(12) United States Patent
Kawiecki et al.

(10) Patent No.: US 9,719,967 B2
(45) Date of Patent: Aug. 1, 2017

(54) STRUCTURAL HEALTH MONITORING SYSTEM

(75) Inventors: Grzegorz Marian Kawiecki, Madrid (ES); Rosa Maria Rodriguez, Madrid (ES); Pawel Kudela, Pruszcz Gdansk (PL); Wieslaw Ostachowicz, Gdansk (PL)

(73) Assignee: THE BOEING COMPANY, Chicago, IL (US)

( * ) Notice: Subject to any disclaimer, the term of this patent is extended or adjusted under 35 U.S.C. 154(b) by 315 days.

(21) Appl. No.: 13/226,199

(22) Filed: Sep. 6, 2011

(65) Prior Publication Data
US 2012/0203474 A1 Aug. 9, 2012

(30) Foreign Application Priority Data

Feb. 8, 2011 (EP) ..................................... 11382026

(51) Int. Cl.
| | | |
|---|---|---|
| *G01B 5/28* | (2006.01) | |
| *G01B 5/30* | (2006.01) | |
| *G01N 29/07* | (2006.01) | |

(52) U.S. Cl.
CPC ..... *G01N 29/07* (2013.01); *G01N 2291/0258* (2013.01); *G01N 2291/103* (2013.01); *G01N 2291/2694* (2013.01)

(58) Field of Classification Search
CPC ... G06F 17/00; G06F 17/18; G01N 2203/005; G01N 2291/106; G01N 2203/0055; G01N 29/07
(Continued)

(56) References Cited

U.S. PATENT DOCUMENTS

| 6,799,126 B1* | 9/2004 | Ratcliffe et al. ................. 702/56 |
| 7,024,315 B2* | 4/2006 | Giurgiutiu ....................... 702/33 |

(Continued)

FOREIGN PATENT DOCUMENTS

| CN | 1804611 A | 7/2006 |
| CN | 1865980 A | 11/2006 |

(Continued)

OTHER PUBLICATIONS

Staszewski, "Intelligent signal processing for damage detection in composite materials", Composites Science and Technology, vol. 62, No. 7-8, 2002, pp. 941-950.

(Continued)

*Primary Examiner* — Gregory J Toatley
*Assistant Examiner* — Eman Alkafawi
(74) *Attorney, Agent, or Firm* — Yee & Associates, P.C.

(57) ABSTRACT

The present invention relates to a structural health monitoring system, for example a system used in the non-destructive evaluation of an aircraft structure. The present invention provides a method and apparatus for evaluating one or more anomalies within a structure using a structural health monitoring system that includes at least three transducers arranged in operative contact with the structure such that no two transducers are aligned to be parallel. A transducer excites an elastic wave that propagates through the structure, and reflections from any anomalies within the structure are collected by the three transducers. These collected signals are analyzed to identify an anomaly within the structure. Time of flight techniques are used to determine the location of the anomaly.

20 Claims, 10 Drawing Sheets

(58) Field of Classification Search
USPC ..... 702/39, 34, 35, 40, 66, 81, 84, 104, 134
See application file for complete search history.

(56) References Cited

U.S. PATENT DOCUMENTS

| | | | | |
|---|---|---|---|---|
| 8,069,011 | B2* | 11/2011 | Liu et al. | 702/181 |
| 8,327,709 | B2* | 12/2012 | Daraio et al. | 73/632 |
| 2003/0009300 | A1 | 1/2003 | Giugiutiu | |
| 2006/0101918 | A1* | 5/2006 | Pena et al. | 73/632 |
| 2006/0136359 | A1* | 6/2006 | Wilt et al. | 707/1 |
| 2007/0017297 | A1* | 1/2007 | Georgeson et al. | 73/801 |
| 2008/0183403 | A1* | 7/2008 | Cipra | 702/34 |
| 2009/0016597 | A1* | 1/2009 | Hughes et al. | 382/149 |
| 2009/0079301 | A1* | 3/2009 | Grohmann et al. | 310/332 |
| 2009/0326834 | A1* | 12/2009 | Sundaresan et al. | 702/34 |
| 2010/0079258 | A1* | 4/2010 | Ihn | G01N 29/043 340/10.41 |
| 2010/0217544 | A1* | 8/2010 | Yan et al. | 702/56 |

FOREIGN PATENT DOCUMENTS

| | | |
|---|---|---|
| CN | 101438150 A | 5/2009 |
| CN | 101424663 A | 7/2009 |
| CN | 101923072 A | 12/2010 |
| EP | 1659400 A1 | 5/2006 |
| EP | 1674862 A1 | 6/2006 |
| JP | 2007511741 A | 5/2007 |
| WO | WO2005031502 A2 | 4/2005 |
| WO | WO2009148660 A2 | 12/2009 |

OTHER PUBLICATIONS

Shim et al., "A noise reduction technique for on-line detection and location of partial discharges in high voltage cable networks", Meas. Sci. Technol., vol. 11, Sep. 2000, pp. 1708-1713.

Major et al., "De-noising of two-dimensional angular correlation of positron annihilation radiation data using Daubechies wavelet thresholding", J. Phys.: Condens., Matter 9, Jul. 1997, pp. 10293-10299.

Konstantindis et al., "An Investigation Into the Temperature Stability of a Guided Wave Structural Health Monitoring System Using Permanently Attached Sensors", IEEE Sensors Journal, vol. 7, No. 5, May 2007, pp. 905-912.

Lu et al., "A Methodology for Structural Health Monitoring with Diffuse Ultrasonic Waves in the Presence of Temperature Variations", Science Direct, Ultrasonics vol. 43, Jun. 2005, pp. 717-731.

Kawiecki et al., "Rosette piezotransducers for damage detection", Institute of Physics Publishing, Smart Mater. Struct. vol. 11, Apr. 2002, pp. 196-201.

Smart Material Corporation, 1990 Main Street, Suite 750, Sarasota, Florida 34236, USA, web site retrieved Aug. 4, 2011 http://www.smart-material.com/.

Hibbeler, Mechanics of Materials, Prentice Hall, Inc., 1997, web site retrieved Aug. 4, 2011 http://books.google.com/books/about/Mechanics_of_materials.html?id=B6RRAAAAMAAJ.

Matt et al., "Macro-fiber composite piezoelectric rosettes for acoustic source location in complex structures", Smart Materials and Structures, Smart Mater. vol. 16, Jul. 2007, pp. 1489-1499.

State Intellectual Property Office of Peoples Republic of China Office Action, dated Nov. 14, 2016, regarding Application No. 201210026055.0, 5 pages.

Canadian Intellectual Property Office Office Action, dated Nov. 25, 2013, regarding Application No. 2,763,220, 3 pages.

Notices of Reasons for Rejection and English Translation, issued Nov. 4, 2015, regarding Japanese Patent Application No. 2012-021699, 5 pages.

State Intellectual Property Office of Peoples Republic of China Third Office Action, dated May 16, 2016, regarding Application No. 201210026055.0, 23 pages.

State Intellectual Property Office of Peoples Republic of China Office Action, dated Mar. 20, 2015, regarding Application No. 201210026055.0, 9 pages.

State Intellectual Property Office of Peoples Republic of China Notification of Fifth Office Action, dated Feb. 16, 2017, regarding Application No. 201210026055.0, 10 pages.

* cited by examiner

STRUCTURAL HEALTH MONITORING SYSTEM

FIELD OF THE INVENTION

The present invention relates to a structural health monitoring system, for example a system used in the non-destructive evaluation of a structure such as an aircraft structure.

BACKGROUND OF THE INVENTION

Structural health monitoring systems are attracting more and more interest. They provide a non-destructive method of evaluating the integrity of a structure. For example, use of structural health monitoring systems in the aerospace industry is becoming more widespread.

This is because such systems provide a non-invasive method of evaluating the health of an aircraft (or certain of its components) that is generally quicker and less expensive to perform than traditional counterparts. Moreover, the incorporation of structural health monitoring systems may allow longer intervals between service inspections, and may allow a lengthened service life of the aircraft.

Structural health monitoring systems have been used with both metal (e.g. aluminium and aluminium alloys) and composite structures.

Structural health monitoring systems comprising arrays of transducers, such as piezoelectric transducers, that monitor the propagation of elastic waves through a structure are known. Anomalies within the structure reflect the elastic waves, and these reflections are detected by the transducers. For example, delamination of resin-fibre composite structures and cracks in both composite and metal structures cause reflections that may be detected.

In addition merely to identifying the presence of one or more anomalies and or at least one anomaly, the location of an anomaly may be determined. For example, it is known to use a distributed array of transducers. Differences in times of arrival of the reflected wave at the transducers are converted to an equivalent distance from each transducer, from which the position of the anomaly may be determined using triangulation.

However, these systems are expensive and time consuming to install due to the large number of distributed sensors that must be provided and located. Furthermore, the large number of sensors results in a weight penalty for the aircraft, and also affects the basic parameters of the structure such as its inertia distribution and stiffness.

An alternative to a distributed array of transducers is to use a phased array of transducers. In such an array, the transducers are located in close proximity to one another. As is well understood in such applications as phased array antennas, the transducers are excited using an excitation signal whose phase varies between the transducers, thereby effecting beam steering. The transducers listen for reflected signals, and determine the location of one or more anomalies and or at least one anomaly by using the measured time of flight of the reflection and the known direction of propagation.

However, such phased-array systems also suffer from disadvantages. The beam-steering technique relied upon with phased arrays requires complex signal processing to extract directional information. Moreover, such systems suffer from signal leaks to the sides of the array such as grating lobes, along with strong secondary signals at angles other than the intended steering angle. Also, the required precision in beam forming and steering places exacting requirements on transducer specification and installation.

Hence, the established techniques of distributed arrays and phased arrays of transducers suffer from complexity, and tight manufacturing and design requirements, that increases significantly the expense of fabrication and integration within a structure. The complexity of the data generation and processing further increases cost.

Consequently, there is a need for a structural health monitoring system with reduced complexity, reduced cost and easier installation.

SUMMARY OF THE INVENTION

Against this background and from a first aspect, the present invention provides a method of evaluating damage within a structure using a structural health monitoring system. The structural health monitoring system comprises one or more, or a set of, at least three receivers arranged in operative contact with the structure, and a transmitter also in operative contact with the structure.

The method comprises operating the transmitter to excite an elastic wave that propagates through the structure. The elastic wave may be generated by one element of the at least three or the set of the three receivers, any one or combinations of them, or by a separate transmitter. If separate, the transmitter may be located proximate the set of three receivers.

The method further comprises collecting monitoring signals from the at least three receivers so as to monitor for reflections of the elastic wave from any anomalies within the structure. The monitoring signals are analysed to identify one or more anomalies and or at least one anomaly within the structure.

Thus, the present invention provides a simple system for use in structural health monitoring. The system uses a non-destructive method, and may be applied to all manner of structures like aerospace structures that may be metal or composite. An active system is employed that uses a transmitter to generate an elastic wave, and then detects reflections of the elastic wave using the receivers.

A simple array of one or more, at least three receivers, or as few as three, are used to identify anomalies within the structure. Thus, when compared with known distributed arrays and phased arrays of transducers, fewer transducers are needed. The location of the anomaly may be identified and found by solving a simple set of linear equations, in contrast with the far more complex calculations required for phased arrays. One or more arrays of receivers may be used with a time of flight method to locate an anomaly, or two or more arrays of receivers may be used to locate an anomaly where each array is used to determine the direction to the anomaly.

The transmitters and receivers may be chosen from many suitable choices. For example, the transmitter may be a simple device capable only of transmitting an elastic wave to the structure. The receiving transducers may be capable only of detecting elastic waves travelling in the structure. However, it is preferred for transducers to be used for the transmitter and receivers that could be used to excite and detect elastic waves travelling in the structure. To this end, piezoelectric transducers are particularly preferred, such as macro fibre composite piezoelectric transducers. The transmitter and receivers may be joined to the structure in any suitable way, such as by the methods described in the following specific description.

Optionally, analysing the monitoring signals comprises performing a differencing operation as follows. For each receiver, a reference signal is subtracted from the monitoring signal collected by that receiver. The monitoring signal may be subjected to pre-processing prior to the differencing operation. For example, the monitoring signal may be subjected to filtering, denoising, signal averaging, temperature compensation, and wavelet decomposition.

The reference signal for each receiver may have been collected from the structure at a point in time when it is in a known condition, such as some time before operational service and after manufacture and assembly or during the service life of the structure.

The differencing operation may be any suitable operation, for example a subtraction of the reference signal from the monitoring signal or vice versa, or a division of the monitoring signal by the reference signal or vice versa. The resulting difference signals are then used to identify one or more anomalies and or at least one anomaly within the structure, as it then becomes easier to identify reflection events from amongst noise in the signals. A thresholding technique may be used to identify reflection events, e.g. by looking for peaks above a threshold level.

Analysing the monitoring signal to identify one or more anomalies and or at least one anomaly may comprise calculating the time of flight of reflections found in the difference signals. The time of the signal as it is collected by the three receivers may be referenced to the time of transmission of the elastic wave. Corresponding distances may be calculated from the time of flights so found. The location of the one or more anomalies and or at least one anomaly may be determined and identified from the calculated distances. For example, the location may be ascertained and solved from the calculated distances, and the known and predetermined locations of the transmitter and receivers. If three or more receivers are used, an overdetermined system will result that may optionally be solved to yield a location using a least-squares method.

From another aspect, the present invention resides in a method of evaluating damage within a structure using a structural health monitoring system comprising a pair of arrays. A first array comprises at least three receivers arranged in operative contact with the structure and a transmitter arranged in operative contact with the structure. A second array comprises at least three receivers arranged in operative contact with the structure and a transmitter arranged in operative contact with the structure. The first and second arrays are spaced apart.

The method comprises propagating an elastic wave through the structure using the transmitter of the first array, and collecting monitoring signals from the at least three receivers of the first array to monitor for reflections of the elastic wave from at least one anomaly within the structure. The method further comprises propagating an elastic wave through the structure using the transmitter of the second array, and collecting monitoring signals from the at least three receivers of the second array to monitor for reflections of the elastic wave from at least one anomaly within the structure.

The monitoring signals are analysed to identify the at least one anomaly and to determine a direction from the respective first and second arrays to the at least one anomaly. Optionally, the method comprises using the directions to the anomaly from each of the first and second arrays in combination with the known positions of the arrays on the structure to determine the position of the anomaly in the structure.

The second array may be like the first array, as described above with respect to the first mentioned aspect of the invention, and as modified by any of the optional arrangements described above. For example, the elastic wave may be generated by one element of the at least three or the set of the three receivers, any one or combinations of them, or by a separate transmitter. If separate, the transmitter may be located proximate the set of three receivers. Also the transmitters and receivers may be transducers that could be used to excite and detect elastic waves travelling in the structure. Piezoelectric transducers are particularly preferred, such as macro fibre composite piezoelectric transducers.

Optionally, in each of the first and second arrays, each of the receivers is a piezoelectric transducer with a longitudinal axis and a transverse axis. The receivers are arranged such that no two receivers have aligned longitudinal axes. For each receiver, the monitoring signals may be analysed to determine longitudinal and transverse strain components that are used in combination with the known orientations of the receivers within each array to determine the direction to the anomaly.

From another aspect, the present invention resides in a structural health monitoring system comprising one or more arrays of a transmitter arranged to excite an elastic wave through a structure and one or more, or a set of, or at least three receivers arranged to collect monitoring signals including reflections of the elastic wave from anomalies in the structure, and a controller configured to implement any of the methods described above.

From yet another aspect, the present invention resides in a structural health monitoring system for monitoring a structure comprising: one or more, or a set of, or at least three receivers in operative contact with the structure; a transmitter; wherein the transmitter is configured to excite an elastic wave to propagate through the structure; and a processor operatively coupled to the receivers to collect and process monitoring signals collected from each of the at least three receivers.

The processor is configured to analyse the monitoring signals to identify one or more anomalies and or at least one anomaly within the structure.

Optionally, a transducer provides the transmitter and one of the at least three receivers. The transmitter may be located proximate the at least three receivers. The at least three receivers may be transducers, optionally piezoelectric transducers such as macro fibre composite piezoelectric transducers.

Optionally, the processor is configured to analyse the monitoring signals by performing a differencing operation whereby, for each receiver of the at least three, a reference signal stored in memory is subtracted from the monitoring signal collected by that receiver, and wherein resulting differencing signals are used to identify the at least one anomaly within the structure. The processor may be configured to analyse the monitoring signal and to identify the at least one anomaly by calculating time of flight of the reflections. The processor may be configured to analyse the monitoring signal and to calculate corresponding distances from the calculated time of flights and to determine the location of the at least one anomaly from the calculated distances. The processor may be configured to determine the location of the at least one anomaly by solving the location from the calculated distances using known locations of the transmitter and the at least three receivers.

From another aspect, the present invention resides in a structural health monitoring system for monitoring a structure comprising first and second arrays. A first array includes at least three receivers in operative contact with the structure and a transmitter in operative contact with the structure. A second array includes at least three receivers in operative contact with the structure and a transmitter in operative contact with the structure. The second array is spaced apart from the first array.

The transmitter of the first array is configured to excite an elastic wave to propagate through the structure, and a processor is operatively coupled to the receivers of the first array to collect monitoring signals from each of the at least three receivers. The transmitter of the second array is configured to excite an elastic wave to propagate through the structure, and the processor is operatively coupled to the receivers of the second array to collect monitoring signals from each of the at least three receivers. The processor is configured to analyse the monitoring signals to identify at least one anomaly within the structure and to determine a direction from the respective first and second arrays to the at least one anomaly.

Optionally, the processor is configured to use the directions to the anomaly from each of the first and second arrays in combination with the known positions of the arrays on the structure to determine the position of the anomaly in the structure.

Optionally, a transducer may provide both the transmitter and one of the at least three receivers in either of or both of the first and second arrays. The transmitter may be located proximate the at least three receivers in either of or both of the first and second arrays.

Optionally, the processor is configured to analyse the monitoring signals by performing a differencing operation whereby, for each receiver, a reference signal is subtracted from the collected monitoring signals by that receiver, and wherein resultant differencing signals are used to identify the at least one anomaly within the structure. The structural health monitoring system may be configured to collect reference signals from the structure for each receiver, optionally after the structure is deemed ready for operational use.

Optionally, in each of the first and second arrays, each of the receivers is a piezoelectric transducer with a longitudinal axis and a transverse axis, and wherein the receivers are arranged such that no two receivers have aligned longitudinal axes. For each receiver, the processor may be configured to analyse the monitoring signals to determine longitudinal and transverse strain components and use these components in combination with the known orientations of the receivers within each array to determine the direction to the anomaly.

Other preferred, but optional, features of this structural health monitoring system are set out in the appended claims. Variations of these features may be made as previously described with respect to the method aspect of the invention.

BRIEF DESCRIPTION OF THE DRAWINGS

In order that the present invention may be more readily understood, preferred embodiments will now be described, by way of example only, with reference to the following drawings, in which.

DETAILED DESCRIPTION OF THE INVENTION

Figure 1:
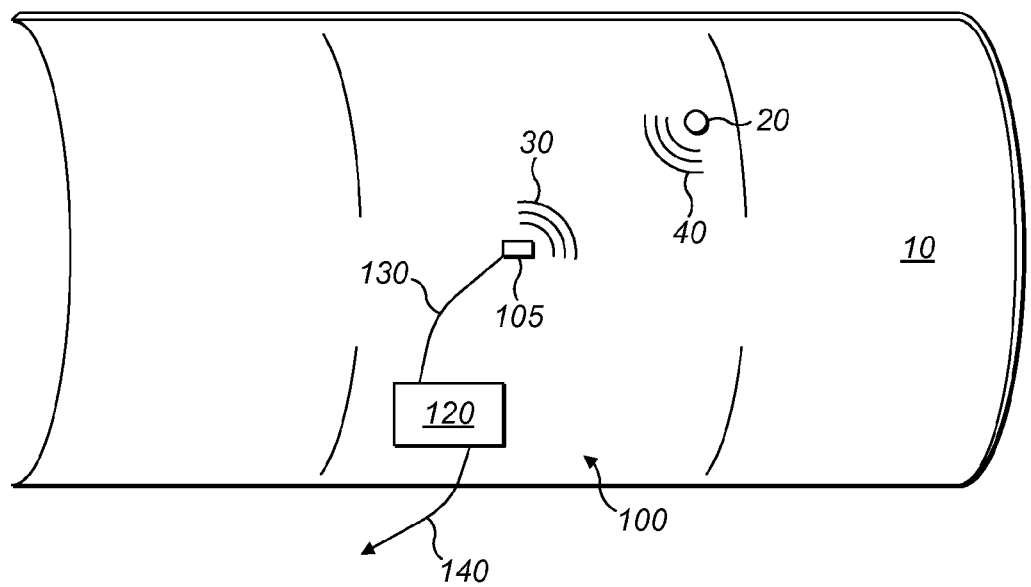
FIG. 1 is a schematic representation of a structural health monitoring system according to an embodiment of the invention installed on a structure.

FIG. 1 shows a structure 10, in this example a resin-fibre composite skin panel for an airplane fuselage. The structure 10 is provided with a structural health monitoring system 100. The structural health monitoring system 100 comprises one or more arrays of transducers 105 fastened to the structure 10. In this example, the transducers 105 are fastened to an interior surface of the structure 10, although the transducers 105 may be fastened to an exterior surface or may be provided within the structure 10 itself. The array of transducers 105 shown in FIG. 1 is connected to a processor 120 via a data connection 130. A further data connection 140 allows data to be forwarded to other connected devices.

The structural health monitoring system 100 monitors the structure 10 for damage such as an area of delamination within the composite structure 10 as may be caused by an object striking the structure 10. The site of the damage is indicated at damage or damage site 20, also referred further herein as anomaly 20 or anomalies 20 in FIG. 1. The structural health monitoring system 100 may be used according to the method illustrated in FIG. 2.

At step 210, a transducer 110 from the array 105 is operated so as to excite an elastic wave that propagates through the structure 10, as shown at site 30 in FIG. 1. As used herein when referring to "transducer 110" without designating "110T" or "110R", it is intended to refer to any of transducers 110T, transducers 110R, or combinations thereof. When the elastic wave impinges on the delaminated section or damage or damage site 20, a portion of the elastic wave will be reflected, as shown at site 40 in FIG. 1. At step 220, the array 105 of transducers 110 is used to collect, obtain, or acquire signals of the elastic waves sensed. These signals will include a contribution from the elastic wave reflected by the damage or damage site 20.

The array 105 of transducers 110 may be used to collect, obtain, or acquire signals over a time-window corresponding to the time taken for the elastic wave to propagate to the furthest edge of the structure 10 and back again (or slightly longer) to ensure all reflection events are captured. At step 230, the signals are analysed and any reflection events indicating one or more anomalies and or at least one anomaly such as damage or damage site 20 within the structure 10 are identified as being indications of potential damage or damage site 20 to the structure 10.

Figure 2:
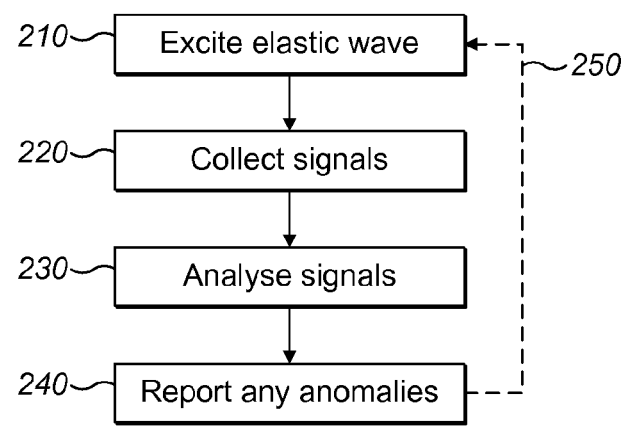
FIG. 2 shows schematically a method of evaluating damage within a structure according to an embodiment of the invention.

At step 240, the anomalies 20 found are reported. The reporting may be visual (for example, as a display on a monitor or the like) or it may correspond to storing the data for later retrieval and inspection (for example, saving a data file providing details of the anomalies 20 found). As indicated at 250, the method may repeat, such that the structure 10 is periodically or continually monitored by the structural health monitoring system 100. The frequency with which the method of FIG. 2 is repeated may be chosen as desired.

The processor 120 of the structural health monitoring system 100 may take many forms, provided it is capable of performing the necessary analysis of the signals provided by the transducers 110. It is preferred for the processor 120 to be capable of sending drive signals to the transducers 105 that excites elastic waves in the structure 10. A suitably programmed computer is a good choice for the processor 120. The processor 120 may be located close to the array 105 of transducers 110, as shown in FIG. 1, or it may be located remote from the array 105 of transducers 110.

The signals from the transducers 110 may be relayed to the processor 120 by a data link or connection 130 of the appropriate length. The data link or connection 130 may be a wired link or it may be wireless. Moreover, it may be a dedicated link or it may be a shared link, for example part of a shared data bus or other network.

Optionally, the processor 120 may have a further data link 140 to allow connection to another device, for example another computer or a display. The data link 140 may be wired or wireless, dedicated or shared.

Different arrangements of the one or more and preferably three or more, transducers 110 within an array 105 are possible. In preferred embodiments, arrays 105 of four transducers 110 are used, of which one is a transmitting transducer 110T and three are receiving transducers 110R. Whether acting as a transmitting transducer 110T or as a receiving transducer 110R, it is currently preferred to use macro fibre composite piezoelectric transducers, like those available from Smart Material Corporation, 1990 Main Street, Suite 750, Sarasota, Fla. 34236, USA. Such transducers are capable of both transmitting and detecting elastic waves. How the transducers 110 are arranged on the structure 10 can be tailored according to where they are to be attached.

Figure 3:
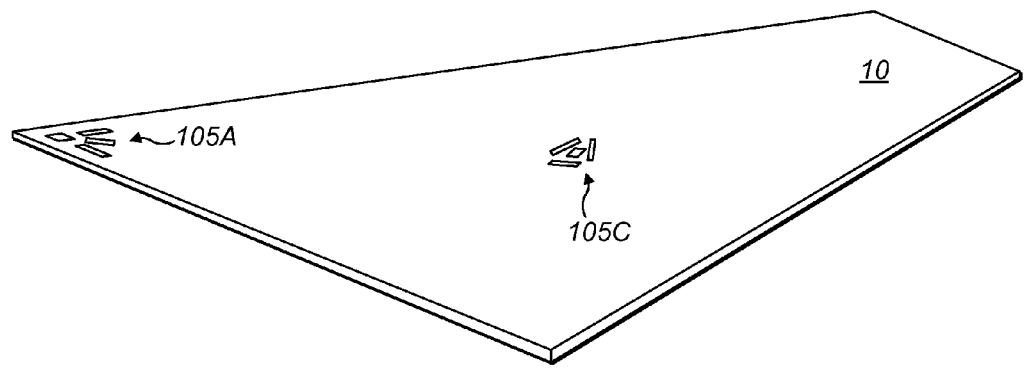
FIG. 3 is a schematic representation of a structure with two arrays of transducers.
Figure 4A:
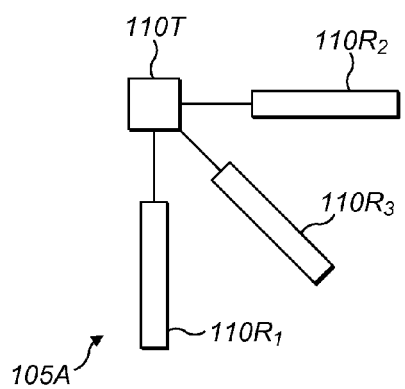
FIGS. 4A to 4D show four exemplary arrangements of arrays of transducers, including arrays like those shown in FIG. 3.
Figure 4B:
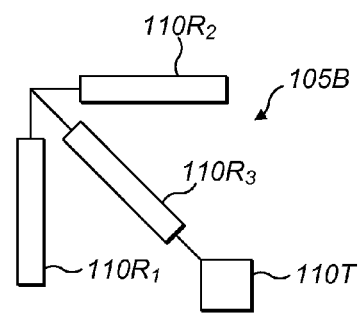

FIG. 3 shows a second example of a structure 10, this time a wing skin panel for an airplane. The structure 10 is shown with two arrangements of arrays 105 of transducers 110. A first arrangement of an array 105A is shown that comprises transducers 110 placed near a corner of the structure 10. A second arrangement of an array 105C is shown that comprises transducers 110 placed centrally on the structure 10. FIGS. 4A-D show four exemplary arrangements of arrays 105A-D of transducers 110R,T. The arrangements 105A and 105B of FIGS. 4A and 4B are better suited to corner positions on a structure 10, whereas arrangements 105C and 105D are better suited to central positions.

FIGS. 4A-D show receiving transducers 110R that have rectangular cross-sections. The rectangular cross-section corresponds to the longitudinal and transverse axes of the receiving transducer 110R. In all four arrangements shown in FIGS. 4A-D, the receiving transducers 110R have their longitudinal axes extending in different directions such that no two transducers 110R are aligned to be parallel. However, in other contemplated embodiments, two or more receiving transducers 110R may extend in parallel.

FIG. 4A shows an array 105A that includes three receiving transducers 110R and one transmitting transducer 110T. The receiving transducers 110R are arranged such that no two receiving transducers 110R are parallel. A first pair of receiving transducers $110R_1$ and $110R_2$ are arranged at right angles to one another, with the third receiving transducer $110R_3$ bisecting the right angle.

As shown in FIG. 3, the receiving transducers 110R may be positioned such that the two receiving transducers $110R_1$ and $110R_2$ forming the right angle extend generally in the direction of the edges of the structure 10 forming the corner and with the third receiving transducer $110R_3$ pointing towards the centre of the structure 10. The transmitting transducer 110T is positioned proximate the three ends of the receiving transducers 110R where they meet.

FIG. 4B shows an arrangement 105B that is similar to the arrangement of FIG. 4A. The three receiving transducers 110R have the same orientation, but the transmitting transducer 110T is moved to be proximate the other end of the bisecting transducer $110R_3$. That is to say, the transmitting transducer 110T is adjacent an end of the receiving transducer $110R_3$ that bisects the right angle between the other two receiving transducer $110R_1$ and $110R_2$, namely the end that is remote from the other two receiving transducers $110R_1$ and $110R_2$.

Figure 4C:
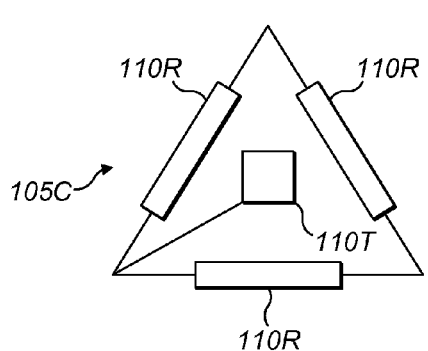
Figure 4D:
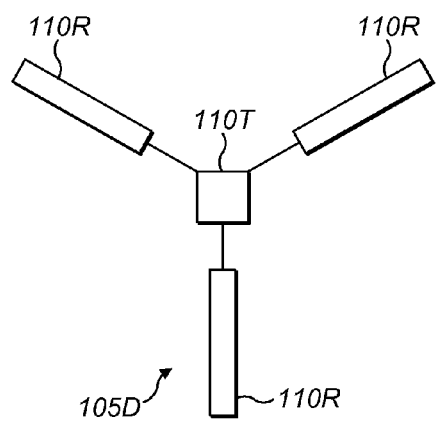

FIG. 4C shows a compact arrangement 105C of four transducers 110. Three receiving transducers 110R are arranged 60° to one another so as to form an equilateral triangle that surrounds a centrally-positioned transmitting transducer 110T. FIG. 4D shows a further arrangement 105D where a central transmitting transducer 110T is positioned between three receiving transducers 110R that radiate outwardly, arranged with angles of 120° between each other. As will be appreciated, in any of the individual arrangements 105A-D, no two receiving transducers 110R are aligned parallel to each other.

Figure 5:
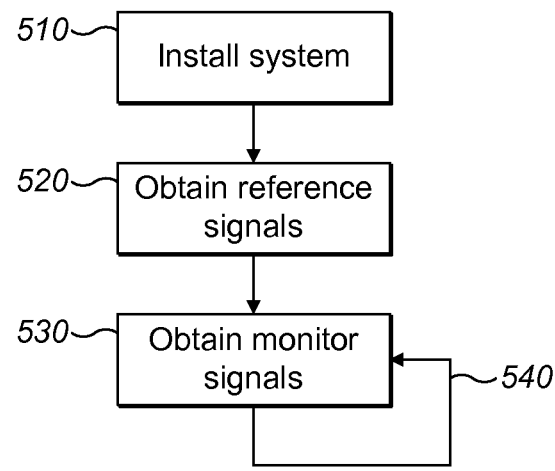
FIG. 5 shows schematically a method of installing a structural health monitoring system and its subsequent use in evaluating the health of the structure which it is affixed.

FIG. 5 shows a method of installing and operating a structural health monitoring system 100 according to the present invention. At 510, the structural health monitoring system 100 is installed in or on a structure 10. This may be performed during the manufacture of the structure 10. For example, if installed in a composite structure, transducers 110 and the associated connections may be laid up with the fibre fabrics and cured within the resin matrix as a composite structure 10 is being fabricated, so as to be an integral part of the structure 10. The wiring may then be connected to the processor 120 that is most likely provided externally.

Alternatively, the one or more, preferably three or more, transducers 110 may be attached to the structure 10 in a number of different ways. The transducers 110 may be surface bonded to the structure 10, affixed using adhesives, fastened to the structure 10 using mechanical fasteners such as screws or rivets, or any other way of providing a firm and enduring attachment.

The transducers 110 may be located within recesses provided in the structure 10, for example at edges or on a surface of the structure 10. The structural health monitoring system 100 may be retrofitted to existing structures 10, for example parts of aircraft already in service.

The transducers 110 may be simply fastened to a surface of the structure 10, either an internal or external surface, or the structure may be modified better to accommodate the transducers 110. For example, if mounted externally, recesses may be formed in the exterior surface of the structure 10 to allow the transducers 110 to be mounted and a flush surface of the structure 10 restored. Locating the transducers 110 internally has advantages in that the transducers 110 are protected from environmental factors like UV radiation and ice, and also in that they do not affect the aerodynamics of the aircraft 50. However, locating the transducers 110 internally may give rise to access issues that make fastening the transducers 110 to an external surface preferable. In addition, some structures 10 may not have internal and external surfaces as such, for example beams.

Returning to the method of FIG. 5, after the structural health monitoring system 100 has been installed at 510, reference signals are collected, or obtained, or acquired at 520 as is described in more detail below with reference to FIG. 6. Essentially, the method is similar to collecting signals once the structure 10 is in use, i.e. a transmitting transducer 110T launches an elastic signal through the structure and receiving transducers 110R record the signals they receive. Preferably, the reference signals are collected, obtained, or acquired once the structure 10 is installed into its final configuration (for example, once a fuselage panel is joined to a complete airplane fuselage).

The reference signals are collected from each receiving transducer 110R for when the structure 10 is in its virgin, undamaged state. Although no anomalies are present, the reference signals will contain reflection events due to the elastic wave being reflected by intended features within the structure 10, such as edges, rivets, fasteners, and joins with stiffeners or other support structures.

The reference signals are stored by the processor 120 for later use during the ongoing operation of the structure 10. The reference signal for each sensor or transducer 110R may have been collected from the virgin structure at a point in time when such structure is in a known condition, such as some time after manufacture and assembly, and before operational service.

It may also be preferable to obtain subsequently new and/or replacement reference signals as the structure endures operational use and periodic maintenance, such as during periodic structural inspection and maintenance periods, as well as at other appropriate times. In this way, such structures can be monitored for changes from a nominal operational condition whether post-manufacture or any other time or instance after which the structure is deemed ready for operational use.

The structure 10 enters service life, and is periodically monitored by the structural health monitoring system 100, as indicated by "obtaining monitor signals" at step 530 and the return loop 540. As previously described with reference to FIG. 2, a transmitting transducer 110T is used to excite an elastic wave that propagates through the structure 10, and the receiving transducers 110R collect, obtain, or acquire monitoring signals that include reflections of the elastic wave. To identify anomalies within the structure 10, the reference signal for the appropriate transducer 110R is subtracted from the monitoring signal to remove (or at least minimise) contributions from intended features and so make more obvious the reflections from any anomalies or damage or damage site 20 within the structure 10.

Figure 6:
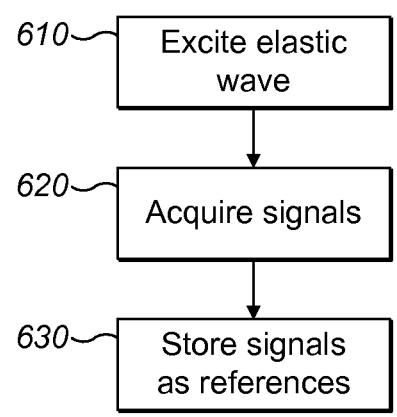
FIG. 6 shows schematically a method of acquiring reference signals.

A method of collecting, obtaining, or acquiring the reference signals will now be described, and is illustrated in FIG. 6. At 610, the processor 120 is used to drive the transmitting transducer 110T by providing a signal that causes the transmitting transducer 110T to oscillate or excite an elastic wave. These oscillations are transmitted to the structure 10, and so propagate through the structure 10. The processor 120 also commands collection, obtaining, or acquiring of the signals produced by the receiving transducers 110R for a specified time period after the elastic wave is excited, as shown at 620.

The propagation of the reflected waves back to the receiving transducers 110R cause the receiving transducers 110R to oscillate and produce a corresponding oscillating electrical signal or signals that is/are collected, obtained, or acquired and stored by the processor 120 as references, as shown at 630. Preferably, the signal to noise ratio in the reference signals is improved by repeating steps 610 and 620, such that a series of elastic waves are excited and reference signals collected, obtained, or acquired each time cumulatively so as to increase statistics.

Structural health monitoring systems 100 according to the present invention may be implemented in different ways. Two currently-preferred embodiments will now be described. The first embodiment employs a time-of-flight method to locate the position of an anomaly or anomalies such as damage or damage site 20, using a single array 105 of transducers 110. The second embodiment employs two or more arrays 105 of transducers 110. Each array 105 of transducers 110 is used to determine a direction to an anomaly or anomalies such as damage or damage site 20. The directions provided by the two or more arrays 105 are used to determine the position of the anomaly or anomalies or damage or damage site 20 through triangulation.

Figure 7:
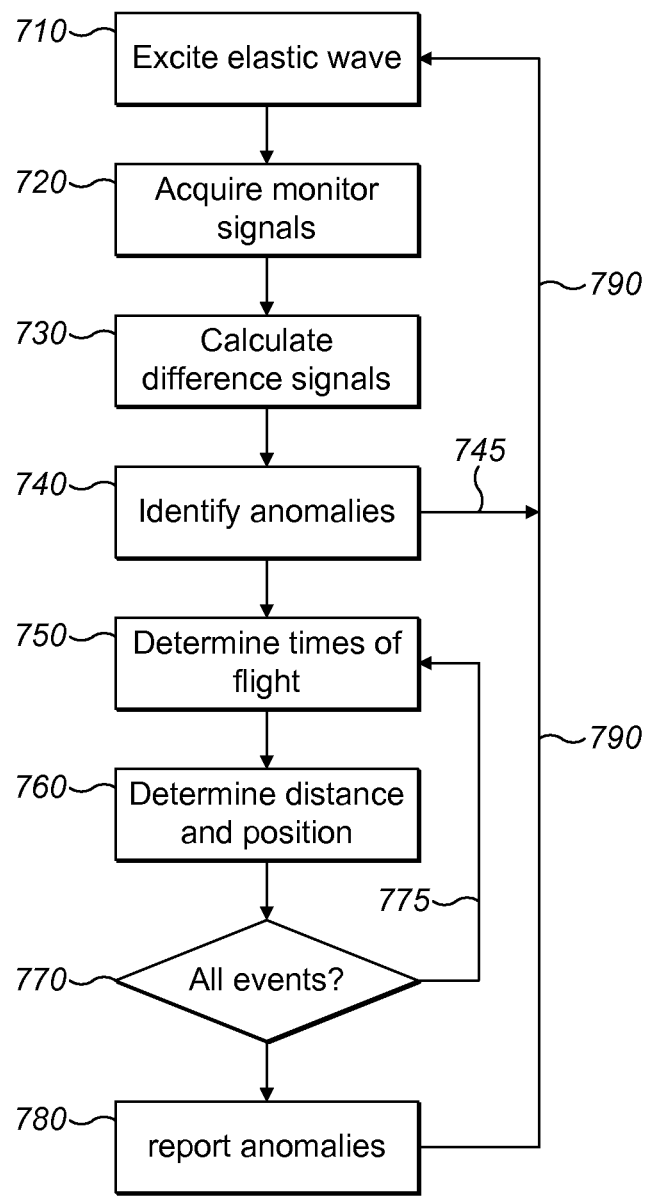
FIG. 7 shows schematically a method of evaluating damage within a structure according to another embodiment of the invention.

FIG. 7 shows in more detail a first method of operating the structural health monitoring system 100 that uses a time-of-flight determination. At 710 the processor 120 excites the transmitting transducer, and launches or excites an elastic wave through the structure 10. The processor 120 then starts monitoring signal acquisition 720, by collecting, obtaining, or acquiring, and storing the monitoring signals produced by the one or more receiving transducers 110R. As described above with respect to FIG. 6, the signal to noise ratio may be improved by repeating steps 710 and 720 to accumulate monitoring signals during propagation of two or more elastic waves.

At 730, the monitoring signal produced by each receiving transducer 110R has the associated reference signal for that transducer 110R subtracted to produce a difference signal or signals. At 740, the processor 120 analyses the difference signals it produced to identify reflection events within the difference signal or signals, and the processor 120 analyses the difference signals it produced to identify anomalies. The method then continues for each reflection event identified as follows.

If no reflection events are detected, the method can loop back to the start 710, via paths 745 and 790. When reflection events are detected, the method continues through steps 750, 760 and 770, and repeats for each reflection event via return loop 775. At step 750, the time of flight for the reflection event in each of the difference signals is determined.

For example, the processor 120 has an associated clock to which launching the elastic wave at 710 and recording or acquiring of the monitoring signals at 720 are referenced. This allows the time elapsed between launch and the reflection event being detected to be determined. At step 760, the processor 120 converts each time of flights found in step 750 to the equivalent distance from the associated transducer 110, and then uses triangulation to determine the distance and position of the anomaly giving rise to the reflection event.

At step 770, the processor 120 checks to determine whether other reflection events require processing, or whether all events have been processed. If yes (all events have not been processed), the method loops back via path 775; or, if not (all events have been processed), the method continues to step 780 where the processor 120 produces a report of the anomalies identified and located. This report may be for immediate display, or may correspond to an accumulation of data, in a data file or the like, for later inspection. For example, the processor 120 may update a data file to add newly discovered anomalies found in the last iteration of the method. Once reporting step 780 is complete, the method loops back along path 790 to return to step 710.

It will be appreciated that the method of FIG. 7 (and the method of FIG. 8 that will be described next) rely on a single array 105 of transducers 110. The position of the anomaly or damage or damage site 20 is found through triangulation of the results from the transducers 110 of the array 105. If more than one array 105 of transducers 110 is provided on the structure 10, each array 105 will determine a position for an anomaly or damage or damage site 20. The positions 30, or also referred to above as site 30, determined for the anomaly or damage or damage site 20 may be combined to provide a single position for the anomaly or damage or damage site 20. Where the arrays 105 are distributed, combining the positions in this way increases accuracy.

Figure 8:
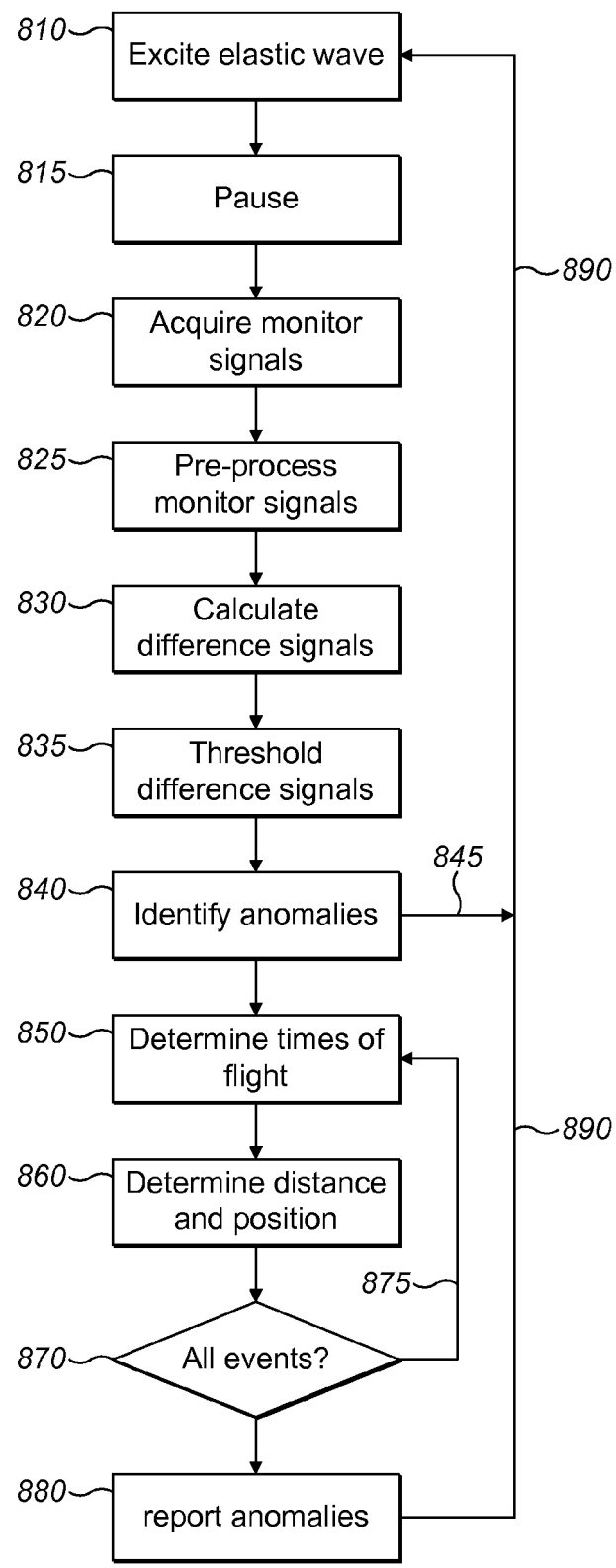
FIG. 8 shows schematically a first method of evaluating damage within a structure according to yet another embodiment of the invention.

FIG. 8 shows a method of operating the structural health monitoring system 100 like that of FIG. 7, although described in greater detail and also including some additional steps.

Steps 810 and 820 largely correspond to steps 710 and 720 of FIG. 7. Hence, an elastic wave is launched or excited at 810 and the monitoring signals are collected, obtained, or acquired at 820. However, a pause is introduced at step 815 such that there is a short delay between the elastic wave being launched and the monitoring signals being collected, obtained, or acquired. This is to ensure the large-amplitude outgoing signal is not detected in the monitoring signals.

At step 830, the processor 120 calculates the difference signals. This is done by subtracting the stored reference signal from the monitoring signal just acquired for each receiving transducer 110R.

In reality, a simple subtraction of the reference signal from the associated monitoring signal is not possible due to the presence of many factors like random noise, temperature effects, and time shifts due to electrical inaccuracy. It is known that subtraction of two signals recorded at different moments in time, and in spite of very similar conditions, will lead to coherent noise, and the present situation is no exception.

In fact, where the signal reflected from damage is weak in intensity, coherent noise levels can be sufficiently high to make damage detection very difficult or sometimes impossible. However, several well-known signal processing techniques may be applied to obtain a high signal to noise ratio, such as filtering, denoising, signal averaging, temperature compensating, wavelet decomposition, etc. A general introduction to selected signal processing techniques is given e.g., by Staszewski W. J., 2002, Intelligent signal processing for damage detection in composite materials, Composites Science and Technology, V. 62, N. 7-8, pp. 941-950. Denoising procedures based on the wavelet analysis are described by Shim I., Soragan J. J. and Siew W. H., 2000, A noise reduction technique for on-line detection and location of partial discharges in high voltage cable networks, Meas. Sci. Technol., V. 11, pp. 1708-1713 and Major A. G., Fretwell H. M., Dugdale S B, Rodriguez-Gozalez A. R. and Alam M. A., 1997, De-noising of two-dimensional angular correlation of positron annihilation radiation data using Daubechies wavelet thresholding, J. Phys.: Condens. Matter, V. 9, pp. 10293-10299. Temperature compensation techniques are described, e.g., by Konstantindis G., Wilcox P. D. and Drinkwater B. W., 2007, An Investigation Into the Temperature Stability of a Guided Wave Structural Health Monitoring System Using Permanently Attached Sensors, IEEE Sensors Journal, V. 7, No. 5, pp. 905-912 and Lu Y. and Michaels J. E., 2005, A Methodology for Structural Health Monitoring with Diffuse Ultrasonic Waves in the Presence of Temperature Variations, Ultrasonics, V. 43, pp. 717-731.

Selection of these techniques may be made to provide the desired accuracy in the results obtained, as is well known in the art. This pre-processing of the monitoring signals is performed at step 825. Once the monitoring signal has been pre-processed at 825, the subtraction is performed at 830.

At step 835, the difference signals are subjected to a thresholding operation by the processor 120, as will now be described by reference to the array 105 of transducers 110 shown in FIG. 11. As can be seen, the array 105 corresponds to the array 105C shown in FIG. 4C. Thus, three receiving transducers 110R are surface-bonded to a structure 10 at angles of 60 degrees to one another to form an equilateral triangle, with the transmitting transducer 110T surface-bonded in the centre.

Figure 9:
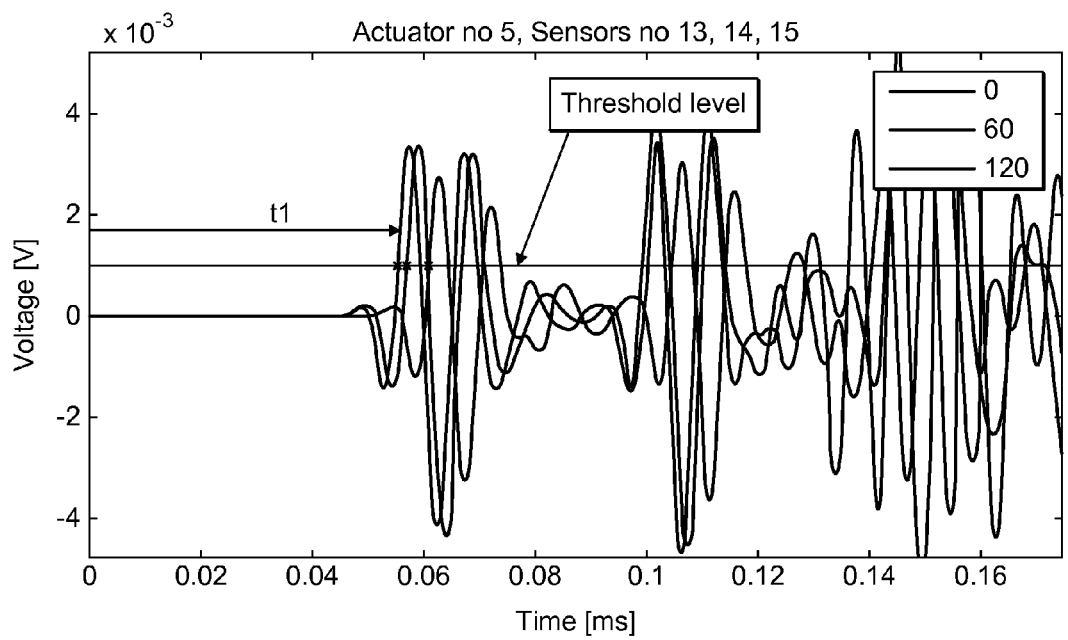
FIG. 9 is a graph showing differential signals produced by transducers of a structural health management system according to an embodiment of the invention.

Such an array may yield difference signals like those shown in FIG. 9. Three difference signals coming from each of the three receiving transducers 110R are shown in FIG. 9, labelled in the legend as 0, 60 and 120. In most situations, reflection events within each monitoring signal arrive at each receiving transducer 110R with a different time shift, and this is reflected in the difference signals shown in FIG. 9. The element at 60 degrees is the first one to detect a reflection event from the damage or damage site 20 in the structure 10.

The example of FIG. 9 shows difference signals that were obtained from numerical calculations. Thus the real-world problems discussed above that leads to a need to pre-process the monitoring signals does not apply here. Nonetheless, the damage localisation is potentially still challenging due to the very small differences between the reference and monitoring signals.

To identify reflection events, peaks are selected that exceed a threshold level. An example of a threshold level is shown in FIG. 9. This threshold level may be chosen to be any suitable value, for example the threshold level may be chosen empirically by collecting sample data and inspecting the resulting difference signals to select a threshold level by eye.

At 840, anomalies are identified from the reflection events shown as peaks within the difference signals that exceed the threshold level. If no anomalies are found, the method may loop back to the start at step 810 via 845 and 890.

Figure 10:
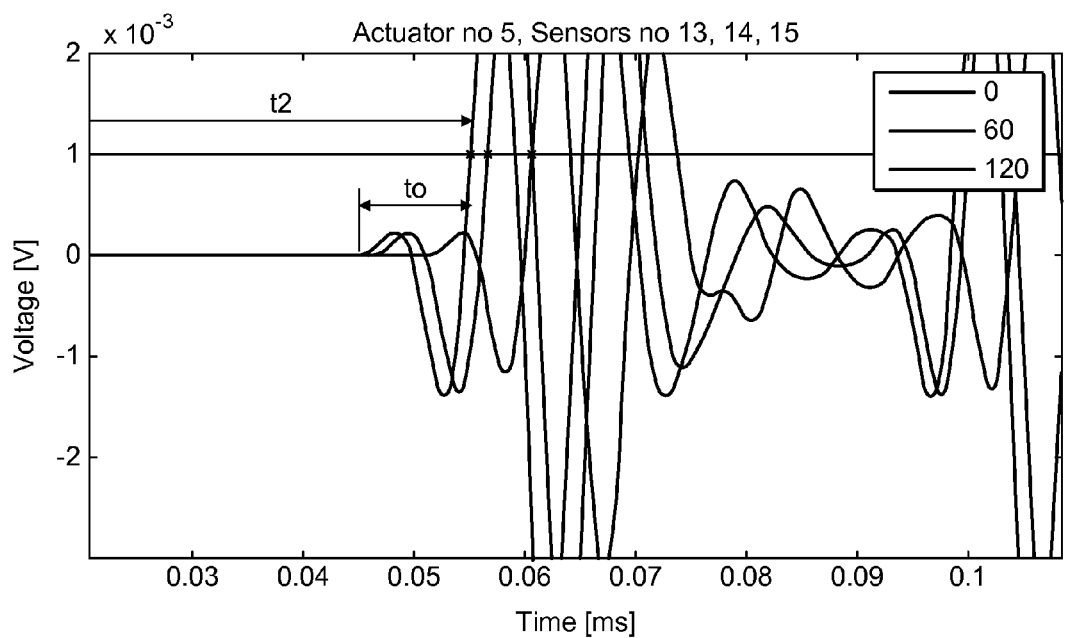
FIG. 10 is a graph showing time of flight corrections for the signals shown in FIG. 9.

Assuming anomalies are identified, the method continues to step 850 where the time of flight is acquired or determined for each reflection event identified in the difference signals of each of the three receiving transducers 110R. The apparent time of flight that may be deduced from when the peak first exceeds the threshold level (shown as t2 in FIG. 10) is advantageously corrected to take into account the real beginning of the associated wave packet that is normally hidden by noise (shown as t0 in FIG. 10).

An appropriate correction $t_0$ can be determined, for example, by a correlation method (by assuming that the reflected wave packet will be similar to the excited wave packet). After the time of flight corrections have been made, the time shifts in the difference signal for each receiving transducer 110R are defined as:

$$\hat{t}_i = t_i - t_0 \quad i=1,2,3 \qquad \text{Eq. (1)}$$

Figure 11:
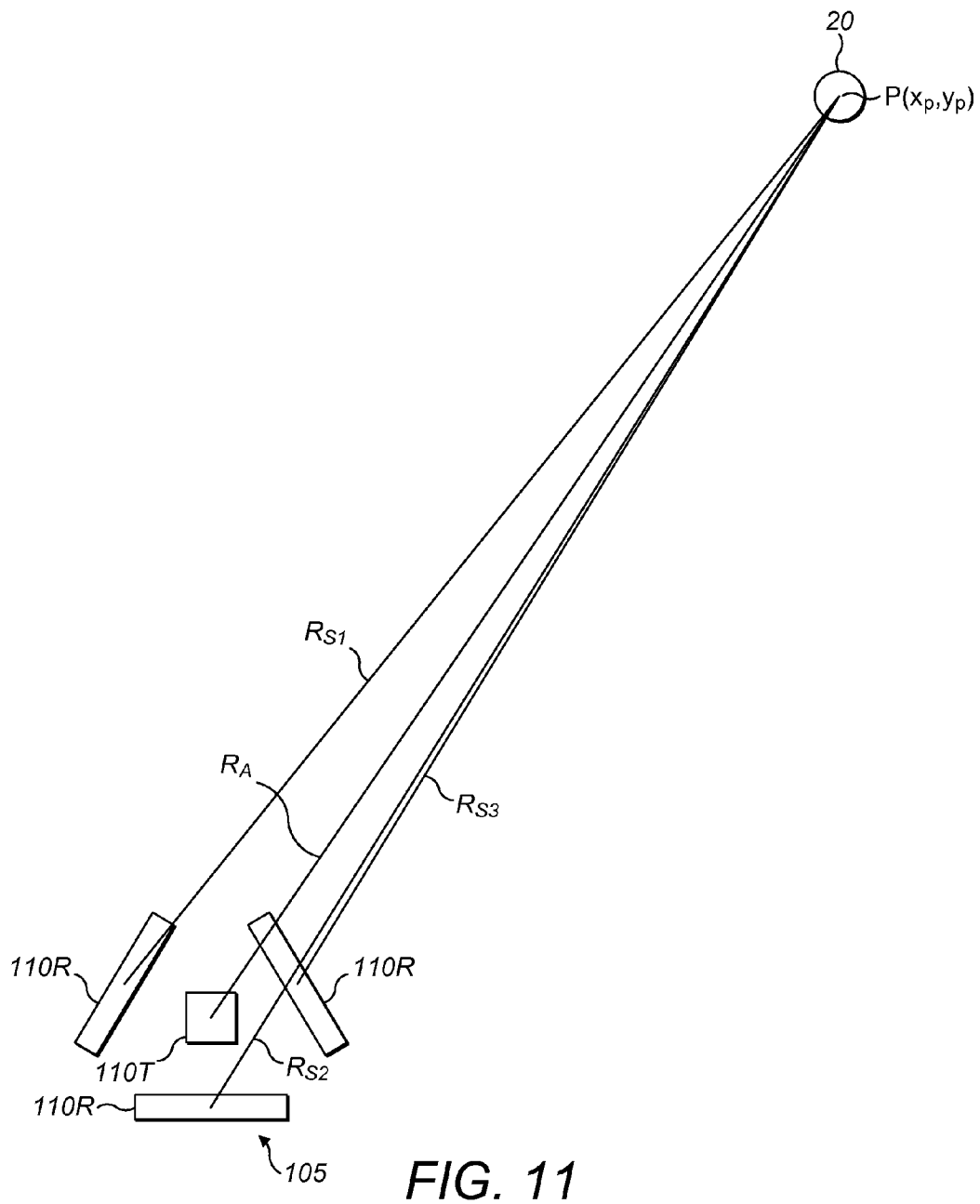
FIG. 11 is a schematic representation to show the distances travelled by waves from an anomaly in a structure to an array of three transducers.

Next, at step 860, the distance travelled by the wave packets as detected by each receiving transducer 110R is determined. These distances are shown in FIG. 11. The distances $R_1$, $R_2$, $R_3$ for a wave packet generated by the transmitting transducer 110T to travel to the anomaly 20 where it will be reflected from point P at co-ordinates ($x_p$, $y_p$), and then to travel back to each of the three receiving transducers 110R are defined as follows.

$$R_1 = R_A + R_{S1}$$
$$R_2 = R_A + R_{S2}$$
$$R_3 = R_A + R_{S3} \qquad \text{Eq. (2)}$$

with $R_A$ being the outbound distance shown in FIG. 11, and $R_{S1}$, $R_{S2}$ and $R_{S3}$ being the inbound distances shown in FIG. 11. These distances are related to the time shifts found in the step 850 according to the following relations.

$$R_1 = \hat{t}_1 c_g$$
$$R_2 = \hat{t}_2 c_g$$
$$R_3 = \hat{t}_3 c_g \qquad \text{Eq. (3)}$$

where $c_g$ is the group velocity of the appropriate propagating mode of the wave packet. With the distances $R_1$, $R_2$ and $R_3$ found, the position of the anomaly 20 may be determined, as follows.

It is assumed that the wave reflected from the anomaly 20 is circular. Accordingly, three circles with a common centre at the location of the anomaly 20 ($x_p$, $y_p$) are defined using Eq. (4).

$$\begin{cases} (x_{S1} - x_p)^2 + (y_{S1} - y_p)^2 = R_{S1}^2 \\ (x_{S2} - x_p)^2 + (y_{S2} - y_p)^2 = R_{S2}^2 \\ (x_{S3} - x_p)^2 + (y_{S3} - y_p)^2 = R_{S3}^2 \end{cases} \qquad \text{Eq. (4)}$$

where $(x_{S1}, y_{S1})$, $(x_{S2}, y_{S2})$, $(x_{S3}, y_{S3})$ are coordinates of the centres of the receiving transducers 110R, and $(x_p, y_p)$ are coordinates of the anomaly 20.

Substituting Eq. (2) into Eq. (4) gives $$\begin{cases} (x_{S1} - x_p)^2 + (y_{S1} - y_p)^2 = (R_1 - R_A)^2 \\ (x_{S2} - x_p)^2 + (y_{S2} - y_p)^2 = (R_2 - R_A)^2 \\ (x_{S3} - x_p)^2 + (y_{S3} - y_p)^2 = (R_3 - R_A)^2 \end{cases} \qquad \text{Eq. (5)}$$

Eq. (5) represents a system of three nonlinear equations with only two unknowns $x_p$ and $y_p$ (there is also the variable $R_A$, but this variable depends on the unknowns $x_p$ and $y_p$). As there are more equations than unknowns, the system is over-determined.

Thus, it is apparent that an array 105 of transducers 110 having just two transducers 110 may be used to provide a location of the anomaly or damage or damage site 20, although such a system may not provide an unambiguous location in all instances, and the present invention encompasses such arrangements. However, it is preferred to use three or more transducers 110 to ensure unambiguous determination of the location of the anomaly or damage or damage site 20, and to provide an over-determined system that provides increased accuracy in determining the position of the anomaly or damage or damage site 20.

Optimisation techniques may be used to solve over-determined systems. For example, a least-square solution of the over-determined system may be obtained by minimizing the following functional:

$$F = [(x_{S1} - x_p)^2 + (y_{S1} - y_p)^2 - (R_1 - R_A)^2]^2 + \\ [(x_{S2} - x_p)^2 + (y_{S2} - y_p)^2 - (R_2 - R_A)^2]^2 + \\ [(x_{S3} - x_p)^2 + (y_{S3} - y_p)^2 - (R_3 - R_A)^2]^2 \qquad \text{Eq. (6)}$$

The solution for $(x_p, y_p)$, i.e. the location of the anomaly 20 in the structure 10, is obtained numerically and identified in this way.

It will be appreciated from the equations above that there is no requirement for each transducer 110 to be aligned in a different direction. Thus, with this method, two or more transducers 110 may be aligned, i.e. their longitudinal and transverse axes may extend to be parallel.

With the position of the anomaly or damage or damage site 20 now found by step 860 of FIG. 8, the method continues to step 870 where a check is made to ensure that all anomalies or events have been processed (and loop 875 allows further anomalies to be processed). When all anomalies have been processed, the method continues to step 880 where the anomalies are reported, as was previously described for step 780. The method may then loop back to the start via path 890.

A second method of operating a structural health monitoring system 100 will now be described with reference to FIGS. 12 to 14. In this embodiment, the structure 10 to be monitored is provided with two or more arrays 105 of transducers 110. For example, an arrangement of two arrays 105 of transducers 110 like that shown in FIG. 3 may be used.

Figure 12:
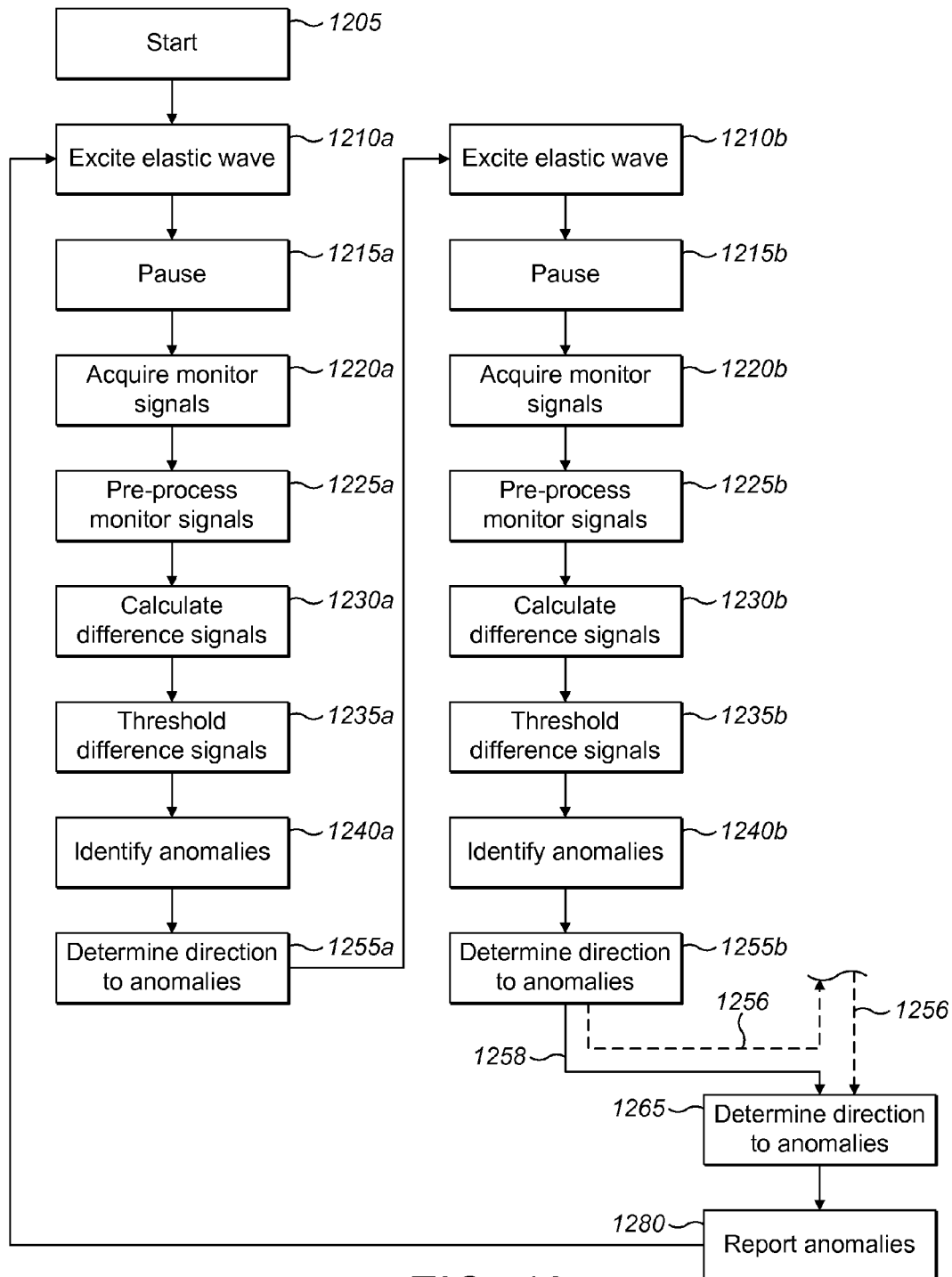
FIG. 12 shows schematically a second method of evaluating damage within a structure according to another embodiment of the present invention.
Figure 13:
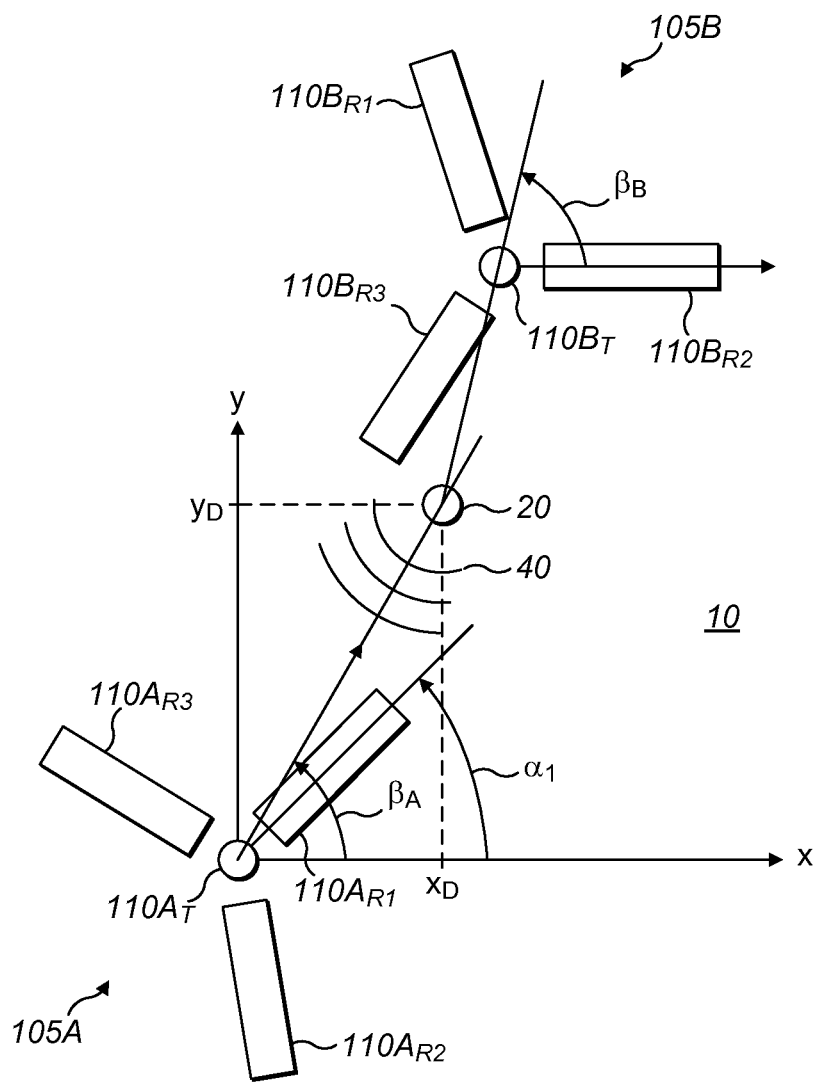
FIG. 13 is a schematic representation of two arrays of transducers and an anomaly in a structure.

FIG. 12 shows the method of operation, and includes many of the steps already described with respect to FIG. 8. The method starts at step 1205, and then proceeds through steps 1210a, 1215a, 1220a, 1225a, 1230a, 1235a and 1240a. As these steps correspond to steps 810, 815, 829, 825, 830, 835 and 840 of FIG. 8, they will only be briefly summarised again.

At step 1210a, an elastic wave is excited using a first array 105 of transducers 110. Monitoring signals are acquired, pre-processed, differenced and thresholded to identify anomalies 20 at step 1240a. At step 1255a, each anomaly 20 identified is taken in turn and the direction from the first array 105 to the anomaly 20 is determined. How this is performed is described below with reference to FIGS. 13 and 14.

With the anomalies or damage or damage site 20 and their directions from the first array 105 of transducers 110 determined, the method proceeds to steps 1210b to 1255b. These steps repeat steps 1210a to 1255a, but in respect of a second array 105 of transducers 110. Hence, the anomalies or damage or damage site 20 are identified and their directions from the second array 105 of transducers 110 are determined.

As indicated by broken arrows 1256, the method may repeat steps 1210 to 1255 for further arrays 105 of transducers 110 (such that three or more sets of data of distances to identified anomalies or damage or damage site 20 are collected, obtained, or acquired).

Although each iteration of steps 1210 to 1255 for each array 105 of transducers 110 is shown to occur sequentially in FIG. 12, one or more iteration may overlap or occur in parallel. For example, steps 1210*b* et seq may be implemented once step 1220*a* has completed, such that the wave excitation and acquiring monitoring signals steps occur sequentially for each iteration, but overlap with the data processing steps of preceding iterations.

Once all data has been gathered, either using two arrays 105 as indicated by arrow 1258 or using more than two arrays 105 as indicated by arrows 1256, the method proceeds to step 1265 where the directions obtained by each array 105 of transducers 110 for each anomaly 20 identified is used to determine the positions of those anomalies 20. This step 1265 is described in more detail below, but essentially relies on the intersection of the pair of the directions to each identified anomaly 20.

Once the positions of the anomalies or damage or damage site 20 have been determined, the anomalies or damage or damage site 20 are reported at step 1280. This step corresponds to step 880 of FIG. 8, and so will not be described again. The method may repeat.

The step 1255 of determining the direction to each anomaly or damage or damage site 20 will now be explained with reference to FIG. 13.

A structure 10 to be monitored is provided with two arrays 105A,B of transducers 110, with each array 105A,B comprising three receiving transducers $110A_{R1-3}$, $110B_{R1-3}$ and a transmitting transducer $110A_T$, $110B_T$. An anomaly 20 is shown, along with an elastic wave 40 reflected from the anomaly 20 towards the first array 105A.

Figure 14:
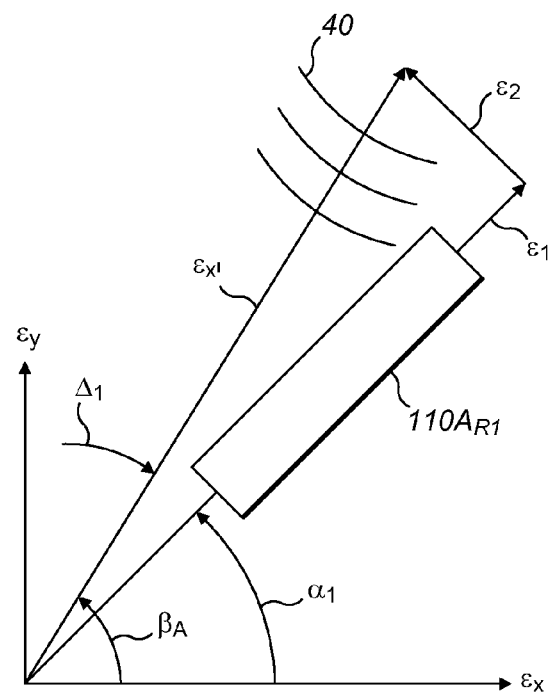
FIG. 14 shows one of the transducers of FIG. 13 in more detail.

Transducer $110A_{R1}$ is shown in greater detail in FIG. 14 such that the longitudinal transverse axes are indicated, along with the strain distribution in the transducer $110A_{R1}$. The wave produced by the transmitting transducer $110A_T$ bounces from the anomaly 20 and generates longitudinal and transverse strain components $\epsilon_1$ and $\epsilon_2$ respectively in each of the receiving transducers $110A_{R1-3}$. Strain components $\epsilon_1$ and $\epsilon_2$ are defined as:

$$\epsilon_1 = \epsilon_{x'} \cos^2 \Delta \quad \text{Eq. 7}$$

and $$\epsilon_2 = \epsilon_{x'} \sin^2 \Delta \quad \text{Eq. 8}$$

where $\Delta$ is the angle between the longitudinal axis of the transducer $110A_{R1}$ and the direction of the incoming wave 40, i.e. $\beta - \alpha$ in FIG. 14.

The signal generated at the receiving transducers $110A_{R1-3}$ can be computed as $$V^1 = S_1 \epsilon_1^{\,1} + S_2 \epsilon_2^{\,1}$$

$$V^2 = S_1 \epsilon_1^{\,2} + S_2 \epsilon_2^{\,2}$$

$$V^3 = S_1 \epsilon_1^{\,3} + S_2 \epsilon_2^{\,3} \quad \text{Eq. 9}$$

where the sensitivity factors $S_1$ and $S_2$ depend on the relation between transducer length and elastic wavelength and on the relative orientation of the receiving transducer $110A_{R1-3}$ and elastic wave direction impingement.

Note that $$\frac{V}{S_1} = \varepsilon_1 + K_T \varepsilon_2 \quad \text{Eq. 10}$$

where the transverse sensitivity ratio $K_T$ is defined as $$K_T = \frac{S_1}{S_2} = \frac{l(d_{31}v_{31}E_2 + d_{32}E_2)\sin(kb/2)}{b(d_{31}E_1 + d_{32}v_{12}E_2)\sin(kl/2)} \quad \text{Eq. 11}$$

where l and b are the length and width of the receiving transducer $110A_{R1-3}$ respectively, k is the wave number, $d_{31}$ and $d_{32}$ are piezoelectric constants of the receiving transducer $110A_{R1-3}$ and $E_1$ and $E_2$ the Young's moduli along the longitudinal and transverse directions.

The plain strain components at the array centre may be computed using the classical relationships derived for strain gauge rosettes (see Mechanics of Materials by R. C. Hibbeler, published by Prentice Hall, Inc. in 1997). The strain transformation equation for determining the strain state in a x'y' coordinate system rotated by a with respect to a reference xy system is:

$$\epsilon_{x'} = \epsilon_x \cos^2 \alpha + \epsilon_y \sin^2 \alpha + \gamma_{xy} \sin \alpha \cos \alpha$$

$$\epsilon_{y'} = \epsilon_x \sin^2 \alpha + \epsilon_y \cos^2 \alpha - \gamma_{xy} \sin \alpha \cos \alpha$$

$$\gamma_{x'y'} = 2(\epsilon_y - \epsilon_x)\sin \alpha \cos \alpha + \gamma_{xy}(\cos^2 \alpha - \sin^2 \alpha) \quad \text{Eq. 12}$$

In a similar manner, the plain strain components can be determined from the response of the three receiving transducers $110A_{R1-3}$:

$$\begin{bmatrix} \varepsilon_x \\ \varepsilon_y \\ \gamma_{xy} \end{bmatrix} = [T]^{-1} \begin{bmatrix} \dfrac{V^1}{S_1} \\ \dfrac{V^2}{S_2} \\ \dfrac{V^3}{S_3} \end{bmatrix} \quad \text{Eq. 13}$$

where the transformation matrix can be written as:

$$[T] = \begin{bmatrix} \cos^2\alpha_1 + K_T\sin^2\alpha_1 & \sin^2\alpha_1 + K_T\cos^2\alpha_1 & (1-K_T)\sin\alpha_1\cos\alpha_1 \\ \cos^2\alpha_2 + K_T\sin^2\alpha_2 & \sin^2\alpha_2 + K_T\cos^2\alpha_2 & (1-K_T)\sin\alpha_2\cos\alpha_2 \\ \cos^2\alpha_3 + K_T\sin^2\alpha_3 & \sin^2\alpha_3 + K_T\cos^2\alpha_3 & (1-K_T)\sin\alpha_3\cos\alpha_3 \end{bmatrix} \quad \text{Eq. 14}$$

The orientation of a perpendicular to the antisymmetric elastic wave front 40, also referred to above as incoming wave 40. (the principal strain angle of the wave) can be defined using another relation known from the strain gauge theory:

$$\tan 2\beta_A = \frac{\gamma_{xy}}{\varepsilon_x - \varepsilon_y} \quad \text{Eq. 15}$$

Please note that the signals collected at a single array 105 are sufficient only to determine the direction β towards the anomaly 20, but not its location. Hence, one or more further arrays 105 are used to find the exact anomaly location. The anomaly location ($y_D$, $x_D$) can be computed using a system of two linear algebraic equations (Matt H. M. and Lanza di Scalea F., 20007, "Maco-fiber composite piezoelectric rosetes for acoustic source location in complex structures," Smart Mater. Struct., V. 16, pp. 1489-1499:

$$y_D = (x_D - x_1)\tan(\beta_1) + y_1 \quad \text{Eq. 16}$$

$$y_D = (x_D - x_2)\tan(\beta_2) + y_2 \quad \text{Eq. 17}$$

where $x_1$, $y_1$ and $x_2$, $y_2$ are the coordinates of the transmitting transducers 110$A_T$ and 110$B_T$.

Where the method of FIG. 12 is performed on a component 10, also referred to above as structure 10, having two or more anomalies or damage or damage site 20, it is possible that "false" anomalies may be detected. This is because the method determines directions from each array 105 of transducers 110 to each anomaly. Hence for each array 105, there may be a number of "directions" radiating from that array 105. Any one "direction" from the array 105 may cross more than one "direction" radiating from another array 105, and the above method identifies all intersections as an anomaly or damage or damage site 20, whereas only a single intersection of each "direction" will be an anomaly or damage or damage site 20.

Time of flight measurements may be used to address this. For example, with the locations of all intersections determined, a transmitting transducer 110T may be used to send out an elastic wave, and reflections are detected by a receiving receiver 110R. Anomalies 20 may be detected in the received signal, and the time of flights determined. These can then be compared to the intersections identified, and intersections with no matching time of flight measurement may be discarded as "false" anomalies.

Both the methods of FIGS. 8 and 12 produce good results. The decision regarding method selection depends on factors such as the space available on the structure 10, the type of structure 10 and the available budget.

A transducer built of three non-directional piezoelements (e.g. disks) would be sufficient to detect and localise damage in simple structures such as aluminium skin panels using time-of-flight methods like those described above. A more complicated implementation, e.g. a set of at least two arrays 105, might perform better for complex structures 10 such as curved carbon composite panels with significant structural damping.

The accuracy of measurements will depend, among other things, on the accuracy of transducer manufacturing. A brief look at equations 13 and 14 reveals that the arrays 105 used for the method of FIG. 12 must contain no parallel receiving transducers 110R. Any parallelism would result in a singular transformation matrix T (see equation 14). Assuming that this is not the case and each of the receiving transducers 110R is affixed at a different angle, their relative orientation and the possible scatter in their geometry matters little, as long as the geometry is known.

Figure 15:
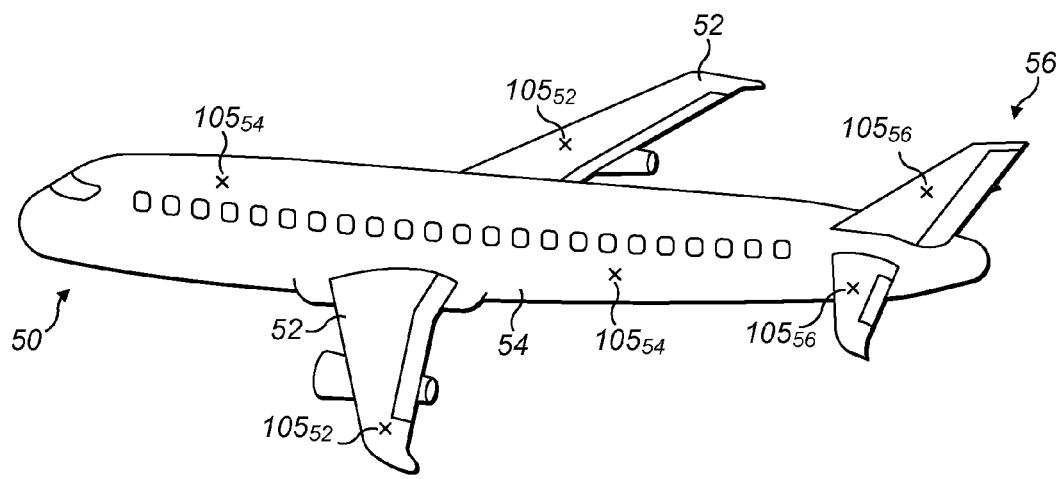
FIG. 15 shows an aircraft fitted with, and possible locations for, structural health monitoring systems according to the present invention.

FIG. 15 shows an aircraft 50 fitted with a structural health monitoring system 100. The structural health monitoring system 100 comprises several arrays 105 of one or more and or at least three transducers 110 located throughout the aircraft 50. Arrays 105 of transducers 110 are provided on structures 10 that include the wings 52 as shown at $105_{52}$, on the fuselage 54 as shown at $105_{54}$, and on the empennage 56 as shown at $105_{56}$.

Each array 105 provides signals that are used to identify anomalies within the associated structure 10. A central processor 120 may be provided that operates all the arrays 105, groups of the arrays 105, or each array 105 may have a dedicated processor 120.

Those skilled in the art will appreciate that modifications may be made to the embodiments described above without departing from the scope of the invention that is defined by the appended claims.

For example, FIGS. 4A to 4D show four exemplary arrangements of transducers. Many different arrangements are possible, where the longitudinal and transverse axes of the three receiving transducers 110R may or may not be aligned. In addition, the number of transducers 110 in the array 105 may be varied from one to any number. The transducers 110 may be evenly spaced and/or rotated relative to one another to provide regular patterns, although irregular arrangements where transducers 110 are not evenly spaced and/or rotated relative to one another.

A separate transmitting transducer 110T need not be provided, as one or more of the receiving transducers 110R may be used to launch the elastic wave into the structure 10. Moreover, two or more separate transmitting transducers 110T may be used.

The invention claimed is:

1. A method of evaluating damage within a structure using a structural health monitoring system comprising at least three receivers arranged in direct contact with the structure and a single transmitter arranged in direct contact with the structure and separate from the at least three receivers, the at least three receivers having corresponding longitudinal axes extending in different directions such that no two of the at least three receivers are aligned to be parallel, the method comprising:
propagating an elastic wave through the structure using the single transmitter;
collecting monitoring signals from the at least three receivers to monitor for reflections of the elastic wave from at least one anomaly within the structure; and
analysing the monitoring signals to identify the at least one anomaly.

2. The method of claim 1, wherein analysing the monitoring signals comprises performing a differencing operation wherein, for each receiver of the at least three receivers, a corresponding reference signal is subtracted from corresponding monitoring signals collected by a corresponding receiver of the at least three receives, and wherein resultant differencing signals are used to identify the at least one anomaly within the structure.

3. The method of claim 2, wherein the structure comprises an aircraft component and, further comprising:
collecting reference signals from the aircraft component for each receiver of the at least three receivers, after the aircraft component is deemed ready for operation of the aircraft.

4. The method of claim 1, wherein analysing the monitoring signals to identify the at least one anomaly comprises calculating a corresponding time of flight of corresponding reflections received by each receiver of the at least three receivers.

5. The method of claim 4, wherein analysing the monitoring signals comprises calculating corresponding distances from each of the corresponding time of flights and wherein a location of the at least one anomaly is determined from the corresponding distances.

6. The method of claim 5, wherein determining the location of the at least one anomaly comprises identifying the location from the corresponding distances, a first known location of the single transmitter, and at least a second known location of at least one of the at least three receivers.

7. A method of evaluating damage within a structure using a structural health monitoring system comprising a first array of a first set of at least three receivers arranged in direct contact with the structure, the first set of at least three receivers having corresponding first longitudinal axes extending in different directions such that no two of the first set of at least three receivers are aligned to be parallel, the first array further comprising a first single transmitter arranged in direct contact with the structure in proximity to and separate from the first set of at least three receivers, and the structural health monitoring system further comprising a second array of a second set of at least three receivers arranged in direct contact with the structure, the second set of at least three receivers having corresponding second longitudinal axes extending in different directions such that no two of the second set of at least three receivers are aligned to be parallel, the second array further comprising a second single transmitter arranged in direct contact with the structure in proximity to and separate from the second set of at least three receivers, wherein the first and second arrays are spaced apart from each other, the method comprising:
propagating a first elastic wave through the structure using the first single transmitter of the first array;
collecting a first set of monitoring signals from the first set of at least three receivers of the first array to monitor for first reflections of the first elastic wave from at least one anomaly within the structure;
propagating a second elastic wave through the structure using the second single transmitter of the second array;
collecting a second set of monitoring signals from the second set of at least three receivers of the second array to monitor for second reflections of the second elastic wave from the at least one anomaly within the structure; and
analysing the first set of monitoring signals and the second set of monitoring signals to identify the at least one anomaly and to determine a first direction from the first array to the at least one anomaly and to determine a second direction from the second array to the at least one anomaly.

8. A structural health monitoring system for monitoring a structure, comprising:
a first set of at least three receivers in direct contact with the structure, the first set of at least three receivers having corresponding longitudinal axes extending in different directions such that no two of the first set of at least three receivers are aligned to be parallel;
a first single transmitter in direct contact with the structure in proximity to and separate from the first set of at least three receivers, wherein the first single transmitter is configured to excite a first elastic wave to propagate through the structure; and
a processor directly coupled to the first set of at least three receivers, the processor configured to collect a first set of corresponding monitoring signals from corresponding ones of the at least three receivers, wherein the processor is further configured to analyse the first set of corresponding monitoring signals to identify at least one anomaly within the structure.

9. The structural health monitoring system of claim 8, wherein the processor is further configured to calculate a corresponding time of flight of corresponding reflections received by each receiver of the at least three receivers.

10. The structural health monitoring system of claim 9, wherein the processor is further configured to calculate corresponding distances from each of the corresponding time of flights and wherein a location of the at least one anomaly is determined from the corresponding distances.

11. The structural health monitoring system of claim 10, wherein the processor is further configured to determine the location of the at least one anomaly by identifying the location from the corresponding distances, a first known location of the single transmitter, and at least a second known location of at least one of the at least three receivers.

12. The structural health monitoring system of claim 8 further comprising:
a second set of at least three receivers in direct contact with the structure;
a second single transmitter in direct contact with the structure, wherein the second single transmitter is configured to excite a second elastic wave to propagate through the structure;
wherein the processor is directly coupled to the second set of at least three receivers, the processor configured to collect a second set of corresponding monitoring signals from corresponding ones of the second set of at least three receivers, wherein the processor is further configured to analyse both the first set of corresponding monitoring signals and the second set of corresponding monitoring signals to identify the at least one anomaly within the structure.

13. The structural health monitoring system of claim 12 wherein, for each receiver of the first set of at least three receives and for each receiver of the second set of at least three receivers, a corresponding receiver comprises a corresponding piezoelectric transducer with a corresponding longitudinal axis and a corresponding transverse axis, wherein each corresponding receiver is arranged such that no two receivers have aligned longitudinal axes, and wherein the processor is further configured to determine corresponding longitudinal and transverse strain components that are used in combination with a corresponding known orientation of each corresponding receiver to determine a direction to the anomaly.

14. The method of claim 1 further comprising:
determining plain strain components at the at least three receivers based on the monitoring signals.

15. The method of claim 1, wherein analysing comprises:
using the monitoring signals to generate an overdetermined system of three non-linear equations with two unknowns; and
solving the over-determined system of three non-linear equations to determine a position of the at least one anomaly.

16. The structural health monitoring system of claim 8, wherein the processor, in being configured to analyse, is configured to:
use the monitoring signals to generate an overdetermined system of three non-linear equations with two unknowns; and
solve the over-determined system of three non-linear equations to determine a position of the at least one anomaly.

17. The structural health monitoring system of claim 8, wherein:
the at least three receivers comprise a first receiver having a first end, a second receiver having a second end, and a third receiver having a third end;
the first and third receivers are arranged at a right angle to one another;
the second receiver bisects the right angle; and the transmitter is positioned proximate where the first end, the second end, and the third end meet.

18. The structural health monitoring system of claim 8, wherein:
   the at least three receivers comprise a first receiver having a first end, a second receiver having a second end and a third end opposite the second end, and a third receiver having a fourth end the first end, the second end, and the fourth end converging at about a vertex;
   the first and third receivers are arranged at a right angle to one another;
   the second receiver bisects the right angle; and
   the transmitter is positioned proximate the third end.

19. The structural health monitoring system of claim 8, wherein:
   the at least three receivers comprise a first receiver, a second receiver, and a third receiver;
   the first and the third receivers are arranged at about sixty degrees to each other so as to form about an equilateral triangle that surrounds the transmitter; and
   the transmitter is about centrally positioned within the equilateral triangle.

20. The structural health monitoring system of claim 8, wherein:
   the at least three receivers comprise a first receiver having a first end, a second receiver having a second end, and a third receiver having a third end;
   the first receiver, the second receiver, and the third receiver all radiating outwardly from the transmitter such that the transmitter is proximate the first end, the second end, and the third end; and
   the first receiver, the second receiver, and the third receiver are arranged with angles of one hundred and twenty degrees between each other.

* * * * *

UNITED STATES PATENT AND TRADEMARK OFFICE
CERTIFICATE OF CORRECTION

PATENT NO.         : 9,719,967 B2
APPLICATION NO.    : 13/226199
DATED              : August 1, 2017
INVENTOR(S)        : Kawiecki et al.

It is certified that error appears in the above-identified patent and that said Letters Patent is hereby corrected as shown below:

In the Claims

Column 18, Line 46, Claim 2 change "three receives" to --three receivers--
Column 20, Line 30, Claim 13 change "three receives" to --three receivers--

Signed and Sealed this
Sixth Day of November, 2018

Andrei Iancu
*Director of the United States Patent and Trademark Office*